(12) United States Patent
Nakashima et al.

(10) Patent No.: US 12,186,418 B2
(45) Date of Patent: Jan. 7, 2025

(54) FOAMING COMPOSITION

(71) Applicant: L'OREAL, Paris (FR)

(72) Inventors: Nahoko Nakashima, Kanagawa (JP); Fan Hu, Kanagawa (JP)

(73) Assignee: L'OREAL, Paris (FR)

( * ) Notice: Subject to any disclaimer, the term of this patent is extended or adjusted under 35 U.S.C. 154(b) by 16 days.

(21) Appl. No.: 17/251,009

(22) PCT Filed: Jun. 7, 2019

(86) PCT No.: PCT/JP2019/023589
§ 371 (c)(1),
(2) Date: Dec. 10, 2020

(87) PCT Pub. No.: WO2019/240242
PCT Pub. Date: Dec. 19, 2019

(65) Prior Publication Data
US 2021/0251867 A1    Aug. 19, 2021

(30) Foreign Application Priority Data
Jun. 12, 2018   (JP) .................................. 2018-111736

(51) Int. Cl.
| | |
|---|---|
| A61K 8/42 | (2006.01) |
| A61K 8/04 | (2006.01) |
| A61K 8/34 | (2006.01) |
| A61K 8/37 | (2006.01) |
| A61K 8/44 | (2006.01) |
| A61K 8/46 | (2006.01) |
| A61K 8/60 | (2006.01) |
| A61Q 1/14 | (2006.01) |

(52) U.S. Cl.
CPC .............. *A61K 8/42* (2013.01); *A61K 8/046* (2013.01); *A61K 8/345* (2013.01); *A61K 8/375* (2013.01); *A61K 8/44* (2013.01); *A61K 8/463* (2013.01); *A61K 8/604* (2013.01); *A61Q 1/14* (2013.01); *A61K 2800/28* (2013.01); *A61K 2800/596* (2013.01); *A61K 2800/87* (2013.01)

(58) Field of Classification Search
CPC .......... A61K 8/42; A61K 8/046; A61K 8/345; A61K 8/375; A61K 8/44; A61K 8/463; A61K 8/604; A61K 2800/28; A61K 2800/596; A61K 2800/87; A61K 8/39; A61K 8/442; A61K 8/33; A61Q 1/14
See application file for complete search history.

(56) References Cited

U.S. PATENT DOCUMENTS

| | | |
|---|---|---|
| 2006/0135392 A1 | 6/2006 | Ribery et al. |
| 2015/0250722 A1 | 9/2015 | Allef et al. |
| 2015/0315123 A1 | 11/2015 | Schuch et al. |
| 2015/0335538 A1 | 11/2015 | Bernard et al. |
| 2016/0101036 A1 | 4/2016 | Yamada et al. |
| 2016/0287504 A1 | 10/2016 | Schroeder et al. |

FOREIGN PATENT DOCUMENTS

| | | | |
|---|---|---|---|
| CA | 2762183 A1 | 6/2012 | |
| CN | 1720899 A | 1/2006 | |
| CN | 104918595 A | 9/2015 | |
| CN | 105025876 A | 11/2015 | |
| CN | 107072898 A | 8/2017 | |
| EP | 1618925 A1 | 1/2006 | |
| JP | 2005-075797 A | 3/2005 | |
| JP | 2011-105606 A | 6/2011 | |
| JP | 2016-044180 A | 4/2016 | |
| JP | 2016108262 A * | 6/2016 | |
| WO | WO-2010060896 A1 * | 6/2010 | ............. A61K 8/046 |
| WO | 2014/098265 A1 | 6/2014 | |
| WO | 2015/152420 A1 | 10/2015 | |
| WO | 2017/012087 A1 | 1/2017 | |

OTHER PUBLICATIONS

PE2E machine translation of JP-2016108262-A (Year: 2016).*
Rospatent, Office Action for the corresponding Russian patent application No. 2020143233, dated Aug. 23, 2021, with English translation.
PCT, International Search Report for the corresponding patent application No. PCT/JP2019/023589, dated Sep. 17, 2019.
Database GNPD [Online] MINTEL; Oct. 28, 2013, anonymous: Body and Hair Shower Gel, XP055618090, Database accession No. 2216958.
Database GNPD [Online] MINTEL; Feb. 16, 2018, anonymous: Facial Wash, XP055618099, Database accession No. 5458645.
Database GNPD [Online] MINTEL; Jul. 20, 2017, anonymous: Lemon Shower Gel, XP055618098, Database accession No. 4970839.
Database GNPD [Online] MINTEL; Nov. 18, 2014, anonymous: Extra Soft Foam Gel Refill, XP055618093, Database accession No. 2797765.
Database GNPD [Online] MINTEL; Mar. 24, 2015, anonymous: Pure-re Shampoo, XP055618095, Database accession No. 3071277.
Rospatent, Office Action for the corresponding Russian patent application No. 2020143233, dated Jan. 13, 2022, with English translation.

(Continued)

*Primary Examiner* — Walter E Webb
*Assistant Examiner* — Amanda Michelle Petritsch
(74) *Attorney, Agent, or Firm* — LUCAS & MERCANTI, LLP

(57) ABSTRACT

The present invention relates to a composition comprising: (a) at least one ether oil; (b) at least one amphoteric surfactant chosen from ($C_8$-$C_{24}$)alkyl betaines, ($C_8$-$C_{24}$) alkylamido($C_1$-$C_6$)alkylbetaines, and mixtures thereof; (c) at least one anionic surfactant; (d) at least one polyglyceryl fatty acid ester; and (e) at least one alklypolyglycoside. The composition according to the present invention is stable and capable of forming good form, and can remove make-up well.

14 Claims, No Drawings

(56) References Cited

OTHER PUBLICATIONS

Rospatent, Office Action for the corresponding Russian patent application No. 2020143233, dated Apr. 13, 2021, with English translation.
Make-Up Removing Cleansing Mousse, 1887187, Mintel GNPD, 2012; www.portal.mintel.com; 4 pages.
Cleansing Foam Mist, 2258905, Mintel GNPD, 2013; www.portal.mintel.com; 3 pages.
Office Action for the corresponding Japanese patent application No. 2018-111736, dated Oct. 11, 2022, with English translation.
Tingchang Deng, et al, Fine and Specialty Chemicals, No. 10, Development of Bio-surfactant-Alkyl-polyglucoside, May 2009, pp. 37-41 (the English translation(s) of the Chinese Office Action(s) is/are (a) concise explanation(s) of the relevance).
Office Action dated Oct. 25, 2023, for the corresponding Chinese Patent Application No. 201980050823.6, with English translation.

* cited by examiner

FOAMING COMPOSITION

CROSS REFERENCE TO RELATED APPLICATION

This Application is a 371 of PCT/JP2019/023589 filed on Jun. 7, 2019 which, in turn, claimed the priority of Japanese Patent Application No. 2018-111736 filed on Jun. 12, 2018, both applications are incorporated herein by reference.

TECHNICAL FIELD

The present invention relates to a composition which is capable of forming, preferably a cosmetic composition, and more preferably a cleansing cosmetic composition.

BACKGROUND ART

Currently, most popular make-up removers are of the oil type which can remove all types of make-up well, but provide oily or slimy sensation during application and will drip down through finger due to the low viscosity of oil in the make-up removers.

In order to provide better usability (e.g., no dripping), make-up removers of the forming type have been developed. The make-up removers of the forming type include typically oil, surfactant and water. These forming make-up removers are capable of forming, and have a cleansing action by virtue of the surfactants, which can suspend, for example, the fatty residues and pigments of make-up.

DISCLOSURE OF INVENTION

As noted above, oil itself can provide slimy sensation and drip down, which could be disadvantages in terms of feeling to use and usability. Further, in general, oil is known to function as an anti-foaming agent. However, it is essential for forming make-up removers or cleansing products to include oil to keep high make-up removing efficacy provided by the oil.

Furthermore, it is important for forming make-up removers to form form with good quality in terms of feeling to use.

In addition, stability is also important for forming make-up removers or cleansing products for daily use by consumers.

Thus, there has been a need for a stable forming composition which can form good form and remove makeup well.

An objective of the present invention is to provide a stable forming composition which can form good form and remove makeup well.

The above objective can be achieved by a composition comprising:
(a) at least one ether oil;
(b) at least one amphoteric surfactant chosen from ($C_8$-$C_{24}$)alkyl betaines, ($C_8$-$C_{24}$)alkylamido($C_1$-$C_6$)alkyl-betaines, and mixtures thereof;
(c) at least one anionic surfactant;
(d) at least one polyglyceryl fatty acid ester; and
(e) at least one alklypolyglycoside.

The (a) ether oil may be selected from the group consisting of dicaprylyl ether, dicapryl ether, dilauryl ether, diisostearyl ether, dioctyl ether, nonyl phenyl ether, dodecyl dimethylbutyl ether, cetyl dimethylbutyl ether, cetyl isobutyl ether, and mixtures thereof.

The (a) ether oil may be present in the composition according to the present invention in an amount ranging from 0.1% to 20% by weight, preferably from 1% to 15% by weight, and more preferably from 5% to 10% by weight, with respect to the total weight of composition.

The (b) amphoteric surfactant may be chosen from coco betaine, cocamidopropyl betaine, and mixtures thereof.

The (b) amphoteric surfactant may be present in the composition according to the present invention in an amount ranging from 0.1% to 20% by weight, preferably from 1% to 15% by weight, and more preferably from 3% to 10% by weight, with respect to the total weight of the composition.

The (c) anionic surfactant may be chosen from amino acid derivatives, alkyl ether sulfates, and mixtures thereof.

The (c) anionic surfactant may be present in the composition according to the present invention in an amount ranging from 0.01% to 15% by weight, in particular from 0.1% to 10% by weight, and more particularly from 0.5% to 5% by weight, with respect to the total weight of the composition.

The (d) polyglyceryl fatty acid ester may have a polyglyceryl moiety derived from 2 to 10 glycerins, preferably 2 to 8 glycerins, and more preferably from 2 to 6 glycerins.

The (d) polyglyceryl fatty acid ester may be present in the composition according to the present invention in an amount ranging from 0.1% to 20% by weight, in particular from 1% to 15% by weight, and more particularly from 5% to 10% by weight, with respect to the total weight of the composition.

The (e) alkylpolyglycoside may be selected from the compound of formula (I):

$$R(O)(G)_x \qquad (I)$$

in which the radical R is a linear or branched $C_{10}$-$C_{22}$ alkyl radical, x ranges from 1 to 5 and G is a saccharide residue chosen from the group of glucose, dextrose, saccharose, fructose, galactose, maltose, maltotriose, lactose, cellobiose, mannose, ribose, dextran, talose, allose, xylose, levoglucan, cellulose and starch; and preferably, G is glucose.

The (e) alkylpolyglycoside may be present in the composition according to the present invention in an amount ranging from 0.01% to 15% by weight, preferably from 0.05% to 10% by weight, and more preferably from 0.1% to 5% by weight, with respect to the total weight of the composition.

The composition according to the present invention may further comprise (f) at least one polyol with 5 or more carbon atoms.

The (f) polyol with 5 or more carbon atoms may be present in the composition according to the present invention in an amount of 15% by weight or less, preferably 10% by weight or less, and more preferably 5% by weight or less, relative to the total weight of the composition.

The composition according to the present invention may be a cosmetic composition, preferably a cleansing cosmetic composition, and more preferably a cleansing cosmetic composition for make-up products such as mascaras.

The present invention also relates to a cosmetic product, preferably a cleansing cosmetic product, capable of forming a volume-expanded composition, comprising:
  the composition according to the present invention; and
  a volume-expanded composition dispenser, for delivering the composition in the form of a volume-expanded composition.

The present invention also relates to a cosmetic process for cleansing a keratin substance, preferably skin, comprising the step of applying the composition according to the present invention to the keratin substance. The application may be carried out in the form of a form. Thus, the composition according to the present invention may be in the form of a form, when being applied onto the keratin substance.

BEST MODE FOR CARRYING OUT THE INVENTION

After diligent research, the inventors have discovered that it is possible to provide a stable forming composition which can form good form and remove makeup well.

Thus, the composition according to the present invention comprises:
- (a) at least one ether oil;
- (b) at least one amphoteric surfactant chosen from ($C_8$-$C_{24}$)alkyl betaines, ($C_8$-$C_{24}$)alkylamido($C_1$-$C_6$)alkyl-betaines, and mixtures thereof;
- (c) at least one anionic surfactant;
- (d) at least one polyglyceryl fatty acid ester; and
- (e) at least one alklypolyglycoside.

The composition according to the present invention is stable and capable of forming good form, and can remove make-up well. The term "stable" here means that the composition can maintain uniform appearance and does not cause any phase separation. The "good" form here means form with at least one, preferably all, of the following properties: higher density, elasticity and long lasting.

The composition according to the present invention can have make-up removing ability which is comparable with conventional make-up removers are of the oil type, even if the amount of oil in the composition according to the present invention is smaller than that in the conventional make-up removers.

The composition according to the present invention can be transparent. The transparent aspect can be attractive to users of the composition according to the present invention.

The composition according to the present invention can be easily rinsed off with water. Thus, users of the composition according to the present invention can quickly rinse off the composition from a keratin substance such as skin and eyelashes.

The composition according to the present invention can provide fresh feeling during use (when applying it onto and/or removing it from a keratin substance). Thus, the composition according to the present invention does not provide oily or slimy sensation during use.

The composition according to the present invention can provide less eye discomfort during use.

The composition according to the present invention has good usability such as "no dripping".

[Composition]

The composition according to the present invention includes, at least, the following ingredients:
- (a) at least one ether oil;
- (b) at least one amphoteric surfactant chosen from ($C_8$-$C_{24}$)alkyl betaines, ($C_8$-$C_{24}$)alkylamido($C_1$-$C_6$)alkyl-betaines, and mixtures thereof;
- (c) at least one anionic surfactant;
- (d) at least one polyglyceryl fatty acid ester; and
- (e) at least one alklypolyglycoside.

Hereafter, the composition according to the present invention will be described in a detailed manner.

(Ether Oil)

The composition according to the present invention comprises (a) at least one ether oil. A single type of ether oil may be used, but two or more different types of ether oils may be used in combination.

Here, "oil" means a fatty compound or substance that is in the form of a liquid or a paste (non-solid) at room temperature (25° C.) and under atmospheric pressure (760 mmHg).

The ether oil may be volatile or non-volatile, preferably non-volatile.

It may be preferable to use, as the ether oil, dialkyl ethers such as those represented by the following formula:

$$R^1\text{—}O\text{—}R^2$$

wherein
each of $R^1$ and $R^2$ independently denotes a linear, branched or cyclic $C_{4\text{-}24}$ alkyl group, preferably $C_{6\text{-}18}$ alkyl group, and more preferably $C_{8\text{-}12}$ alkyl group. It may be preferable that $R^1$ and $R^2$ are the same.

As the linear alkyl group, mention may be made of a butyl group, a pentyl group, a hexyl group, a heptyl group, an octyl group, a nonyl group, a decyl group, an undecyl group, a dodecyl group, tridecyl group, a tetradecyl group, a pentadecyl group, a hexadecyl group, a heptadecyl group, an octadecyl group, a nonadecyl group, an eicosyl group, a behenyl group, a docosyl group, a tricosyl group, and an tetracosyl group.

As the branched alkyl group, mention may be made of a 1-methylpropyl group, 2-methylpropyl group, a t-butyl group, a 1,1-dimethylpropyl group, a 3-methylhexyl group, a 5-methylhexyl group, an 1-ethylhexyl group, an 2-ethylhexylgroup, a 1-butylpentyl group, a 5-methyloctyl group, an 1-ethylhexyl group, an 2-ethylhexyl group, a 1-butylpentyl group, a 5-methyloctyl group, a 2-butyloctyl group, an isotridecyl group, a 2-pentylnonyl group, a 2-hexyldecyl group, an isostearyl group, a 2-heptylundecyl group, an 2-octyldodecyl group, a 1,3-dimethylbutyl group, a 1-(1-methylethyl)-2-methylpropyl group, a 1,1,3,3-tetramethyl-butyl group, a 3,5,5-trimethylhexyl group, a 1-(2-methylpropyl)-3-methylbutyl group, a 3,7-dimethyloctyyl group, and a 2-(1,3,3-trimethylbutyl)-5,7,7-trimethyloctyl group.

As the cyclic alkyl group, mention may be made of a cyclohexyl group, a 3-methylcyclohexyl group, and a 3,3, 5-trimethylcyclohexyl group.

It may be preferable that the ether oil be selected from the group consisting of dicaprylyl ether, dicapryl ether, dilauryl ether, diisostearyl ether, dioctyl ether, nonyl phenyl ether, dodecyl dimethylbutyl ether, cetyl dimethylbutyl ether, cetyl isobutyl ether, and mixtures thereof.

It may be more preferable that the ether oil be selected from the group consisting of dicaprylyl ether, dicapryl ether, dilauryl ether, diisostearyl ether, dioctyl ether, and mixtures thereof.

The amount of the ether oil(s) in the composition according to the present invention may be 0.1% by weight or more, preferably 1% by weight or more, and more preferably 5% by weight or more relative to the total weight of the composition.

On the other hand, the amount of the ether oil(s) in the composition according to the present invention may be 20% by weight or less, preferably 15% by weight or less, and more preferably 10% by weight or less relative to the total weight of the composition.

Thus, the amount of the ether oil(s) in the composition according to the present invention may range from 0.1% to 20% by weight, preferably from 1% to 15% by weight, and more preferably from 5% to 10% by weight relative to the total weight of the composition.

(Amphoteric Surfactant)

The composition according to the present invention comprises (b) at least one amphoteric surfactant chosen from ($C_8$-$C_{24}$)alkyl betaines, ($C_8$-$C_{24}$)alkylamido($C_1$-$C_6$)alkyl-betaines, and mixtures thereof. A single type of such amphoteric surfactant may be used, but two or more different types of such amphoteric surfactant may be used in combination.

According to the present invention, the amphoteric surfactant is selected from the group consisting of ($C_8$-$C_{24}$) alkyl betaines, ($C_8$-$C_{24}$)alkylamido($C_1$-$C_6$)alkylbetaines, and mixtures thereof.

In one embodiment, the ($C_8$-$C_{24}$)alkyl group of the ($C_5$-$C_{24}$)alkyl betaines and ($C_8$-$C_{24}$)alkylamido($C_1$-$C_6$)alkyl-betaines may be a ($C_8$-$C_{20}$)alkyl group, and preferably a ($C_8$-$C_{18}$)alkyl group.

In another embodiment, the ($C_1$-$C_6$)alkyl group of the ($C_8$-$C_{24}$)alkylamido($C_1$-$C_6$)alkylbetaines may be a ($C_1$-$C_4$) alkyl group, and preferably a ($C_1$ or $C_2$)alkyl (methyl or ethyl) group.

It may be preferable that the ($C_8$-$C_{24}$)alkyl betaines be ($C_8$-$C_{24}$)alkyl dimethyl glycine such as ($C_8$-$C_{24}$)alkyl-$N^+$ $(CH_3)_2$—$CH_2COO^-$.

It may be preferable that ($C_8$-$C_{24}$)alkylamido($C_1$-$C_6$)alkylbetaines be ($C_8$-$C_{24}$)alkylamidoethyl dimethyl glycine such as ($C_8$-$C_{24}$)alkyl-CONH—$CH_2CH_2$—$N^+(CH_3)_2$—$CH_2COO^-$.

Examples of ($C_8$-$C_{24}$)alkyl betaines include coco betaine, such as the product sold under the name Dehyton AB-30® by the company Cognis, lauryl betaine, such as the product sold under the name Genagen KB® by the company Clariant, oxyethylenated (10 EO) lauryl betaine, such as the product sold under the name Lauryl Ether (10 EO) Betaine® by the company Shin Nihon Rica, or oxyethylenated (10 EO) stearyl betaine, such as the product sold under the name Stearyl Ether (10 EO) Betaine® by the company Shin Nihon Rica.

Examples of ($C_8$-$C_{24}$)alkylamido($C_1$-$C_6$)alkylbetaines include cocamidopropyl betaine, sold under the name Lebon 2000 HG® by the company Sanyo or sold under the name Empigen BB® by the company Albright & Wilson, or lauramidopropyl betaine, sold under the name Rewoteric AMB12P® by the company Witco.

In one embodiment, the amphoteric surfactant may be chosen from coco betaine, lauryl betaine, oxyethylenated (10 EO) lauryl betaine, oxyethylenated (10 EO) stearyl betaine, cocamidopropyl betaine, lauramidopropyl betaine, and mixtures thereof, preferably from lauryl betaine, coco betaine, cocamidopropyl betaine, and mixtures thereof, and more preferably from coco betaine, cocamidopropyl betaine, and mixtures thereof.

The amount of the amphoteric surfactant(s) in the composition according to the present invention may be 0.1% by weight or more, preferably 1% by weight or more, and more preferably 3% by weight or more relative to the total weight of the composition.

On the other hand, the amount of the amphoteric surfactant(s) in the composition according to the present invention may be 20% by weight or less, preferably 15% by weight or less, and more preferably 10% by weight or less relative to the total weight of the composition.

Thus, the amount of the amphoteric surfactant(s) in the composition according to the present invention may range from 0.1% to 20% by weight, preferably from 1% to 15% by weight, and more preferably from 3% to 10% by weight relative to the total weight of the composition.

(Anionic Surfactant)

The composition according to the present invention comprises (c) at least one anionic surfactant. A single type of anionic surfactant may be used, but two or more different types of anionic surfactant may be used in combination.

The anionic surfactants may be chosen in particular from anionic derivatives of proteins of vegetable origin or of silk proteins, phosphates and alkyl phosphates, carboxylates, sulphosuccinates, amino acid derivatives, alkyl sulphates, alkyl ether sulphates, sulphonates, isethionates, taurates, alkyl sulphoacetates, polypeptides, anionic derivatives of alkyl polyglucosides, and their mixtures.

1) Anionic derivatives of proteins of vegetable origin are protein hydrolysates comprising a hydrophobic group, it being possible for the said hydrophobic group to be naturally present in the protein or to be added by reaction of the protein and/or of the protein hydrolysate with a hydrophobic compound. The proteins are of vegetable origin or derived from silk, and the hydrophobic group can in particular be a fatty chain, for example an alkyl chain comprising from 10 to 22 carbon atoms. Mention may more particularly be made, as anionic derivatives of proteins of vegetable origin, of apple, wheat, soybean or oat protein hydrolysates comprising an alkyl chain having from 10 to 22 carbon atoms, and their salts. The alkyl chain can in particular be a lauryl chain and the salt can be a sodium, potassium and/or ammonium salt.

Thus, mention may be made, as protein hydrolysates comprising a hydrophobic group, for example, of salts of protein hydrolysates where the protein is a silk protein modified by lauric acid, such as the product sold under the name Kawa Silk by Kawaken; salts of protein hydrolysates where the protein is a wheat protein modified by lauric acid, such as the potassium salt sold under the name Aminofoam W OR by Croda (CTFA name: potassium lauroyl wheat amino acids) and the sodium salt sold under the name Proteol LW 30 by Seppic (CTFA name: sodium lauroyl wheat amino acids); salts of protein hydrolysates where the protein is an oat protein comprising an alkyl chain having from 10 to 22 carbon atoms and more especially salts of protein hydrolysates where the protein is an oat protein modified by lauric acid, such as the sodium salt sold under the name Proteol OAT (30% aqueous solution) by Seppic (CTFA name: sodium lauroyl oat amino acids); or salts of apple protein hydrolysates comprising an alkyl chain having from 10 to 22 carbon atoms, such as the sodium salt sold under the name Proteol APL (30% aqueous/glycol solution) by Seppic (CTFA name: sodium cocoyl apple amino acids). Mention may also be made of the mixture of lauroyl amino acids (aspartic acid, glutamic acid, glycine, alanine) neutralized with sodium N-methylglycinate sold under the name Proteol SAV 50 S by Seppic (CTFA name: sodium cocoyl amino acids).

2) Mention may be made, as phosphates and alkyl phosphates, for example, of monoalkyl phosphates and dialkyl phosphates, such as lauryl monophosphate, sold under the name MAP 20® by Kao Chemicals, the potassium salt of dodecyl phosphate, the mixture of mono- and diesters (predominantly diester) sold under the name Crafol AP-31® by Cognis, the mixture of octyl phosphate monoester and diester, sold under the name Crafol AP-20® by Cognis, the mixture of ethoxylated (7 mol of EO) 2-butyloctyl phosphate monoester and diester, sold under the name Isofol 12 7 EO-Phosphate Ester® by Condea, the potassium or triethanolamine salt of mono($C_{12}$-$C_{13}$)alkyl phosphate, sold under the references Arlatone MAP 230K-40® and Arlatone MAP 230T-60® by Uniqema, potassium lauryl phosphate, sold under the name Dermalcare MAP XC-99/09® by Rhodia Chimie, and potassium cetyl phosphate, sold under the name Arlatone MAP 160K by Uniqema.

3) Mention may be made, as carboxylates, of:
amido ether carboxylates (AEC), such as sodium lauryl amido ether carboxylate (3 EO), sold under the name Akypo Form 30® by Kao Chemicals;
polyoxyethylenated carboxylic acid salts, such as oxyethylenated (6 EO) sodium lauryl ether carboxylate (65/25/10 $C_{12}$-$C_{14}$-$C_{16}$), sold under the name Akypo Soft 45 NV® by Kao Chemicals, polyoxyethylenated and carboxymethylated fatty acids originating from olive oil, sold under the name Olivem 400® by Biologia E Tecnologia, or oxyethylenated (6 EO) sodium tridecyl ether carboxylate, sold under the name Nikkol ECTD-6NEX® by Nikkol; and
salts of fatty acids (soaps) having a $C_6$ to $C_{22}$ alkyl chain which are neutralized with an organic or inorganic base, such as potassium hydroxide, sodium hydroxide, triethanolamine, N-methylglucamine, lysine and arginine.

4) Mention may in particular be made, as amino acid derivatives, of alkali salts of amino acids, such as:
sarcosinates, such as sodium lauroyl sarcosinate, sold under the name Sarkosyl NL 97® by Ciba or sold under the name Oramix L 30® by Seppic, sodium myristoyl sarcosinate, sold under the name Nikkol Sarcosinate MN® by Nikkol, or sodium palmitoyl sarcosinate, sold under the name Nikkol Sarcosinate PN® by Nikkol;
alaninates, such as sodium N-lauroyl-N-methylamidopropionate, sold under the name Sodium Nikkol Alaninate LN 30® by Nikkol or sold under the name Alanone ALE® by Kawaken, or triethanolamine N-lauroyl-N-methylalanine, sold under the name Alanone ALTA® by Kawaken;
glutamates, such as triethanolamine monococoyl glutamate, sold under the name Acylglutamate CT-12® by Ajinomoto, triethanolamine lauroyl glutamate, sold under the name Acylglutamate LT-12® by Ajinomoto;
aspartates, such as the mixture of triethanolamine N-lauroyl aspartate and triethanolamine N-myristoyl aspartate, sold under the name Asparack® by Mitsubishi;
glycine derivatives (glycinates), such as sodium N-cocoyl glycinate, sold under the names Amilite GCS-12® and Amilite GCK 12 by Ajinomoto;
citrates, such as the citric monoester of oxyethylenated (9 mol) coco alcohols, sold under the name Witconol EC 1129 by Goldschmidt; and
galacturonates, such as sodium dodecyl D-galactoside uronate, sold by Soliance.

5) Mention may be made, as sulphosuccinates, for example, of oxyethylenated (3 EO) lauryl (70/30 $C_{12}/C_{14}$) alcohol monosulphosuccinate, sold under the names Setacin 103 Special® and Rewopol SB-FA 30 K 4® by Witco, the disodium salt of a hemisulphosuccinate of $C_{12}$-$C_{14}$ alcohols, sold under the name Setacin F Special Paste® by Zschimmer Schwarz, oxyethylenated (2 EO) disodium oleamidosulphosuccinate, sold under the name Standapol SH 135® by Cognis, oxyethylenated (5 EO) lauramide monosulphosuccinate, sold under the name Lebon A-5000® by Sanyo, the disodium salt of oxyethylenated (10 EO) lauryl citrate monosulphosuccinate, sold under the name Rewopol SB CS 50® by Witco, or ricinoleic monoethanolamide monosulphosuccinate, sold under the name Rewoderm S 1333® by Witco. Use may also be made of polydimethylsiloxane sulphosuccinates, such as disodium PEG-12 dimethicone sulphosuccinate, sold under the name Mackanate-DC 30 by MacIntyre.

6) Mention may be made, as alkyl sulphates, for example, of triethanolamine lauryl sulphate (CTFA name: TEA lauryl sulphate), such as the product sold by Huntsman under the name Empicol TL40 FL or the product sold by Cognis under the name Texapon T42, which products are at 40% in aqueous solution. Mention may also be made of ammonium lauryl sulphate (CTFA name: ammonium lauryl sulphate), such as the product sold by Huntsman under the name Empicol AL 30FL, which is at 30% in aqueous solution.

7) Mention may be made, as alkyl ether sulphates, for example, of sodium lauryl ether sulphate (CTFA name: sodium laureth sulphate), such as that sold under the names Texapon N40 and Texapon AOS 225 UP by Cognis, or ammonium lauryl ether sulphate (CTFA name: ammonium laureth sulphate), such as that sold under the name Standapol EA-2 by Cognis.

8) Mention may be made, as sulphonates, for example, of α-olefinsulphonates, such as sodium α-olefinsulphonate ($C_{14}$-$C_{16}$), sold under the name Bio-Terge AS-40® by Stepan, sold under the names Witconate AOS Protégé® and Sulframine AOS PH 12® by Witco or sold under the name Bio-Terge AS-40 CG® by Stepan, secondary sodium olefinsulphonate, sold under the name Hostapur SAS 30® by Clariant; or linear alkylarylsulphonates, such as sodium xylenesulphonate, sold under the names Manrosol SXS30®, Manrosol SXS40® and Manrosol SXS93® by Manro.

9) Mention may be made, as isethionates, of acylisethionates, such as sodium cocoylisethionate, such as the product sold under the name Jordapon CI P® by Jordan.

10) Mention may be made, as taurates, of the sodium salt of palm kernel oil methyltaurate, sold under the name Hostapon CT Paté® by Clariant; N-acyl-N-methyltaurates, such as sodium N-cocoyl-N-methyltaurate, sold under the name Hostapon LT-SFS by Clariant or sold under the name Nikkol CMT-30-T® by Nikkol, Sodium Methyl Stearoyl Taurate sold under the name Nikkol SMT® or sodium palmitoyl methyltaurate, sold under the name Nikkol PMT® by Nikkol.

11) The anionic derivatives of alkyl polyglucosides can in particular be citrates, tartrates, sulphosuccinates, carbonates and glycerol ethers obtained from alkyl polyglucosides. Mention may be made, for example, of the sodium salt of cocoylpolyglucoside (1,4) tartaric ester, sold under the name Eucarol AGE-ET® by Cesalpinia, the disodium salt of cocoylpolyglucoside (1,4) sulphosuccinic ester, sold under the name Essai 512 MP® by Seppic, or the sodium salt of cocoylpolyglucoside (1,4) citric ester, sold under the name Eucarol AGE-EC® by Cesalpinia.

For the amino acid derivatives, it is preferable that they are chosen from acyl glycine derivatives or glycine derivatives, in particular acyl glycine salt.

The acyl glycine derivatives or glycine derivatives can be chosen from acyl glycine salts (or acyl glycinates) or glycine salts (or glycinates), and in particular from the following.
i) Acyl glycinates of formula (I):

in which
R represents an acyl group R'C=O, with R', which represents a saturated or unsaturated, linear or branched, hydrocarbon chain, preferably comprising from 10 to 30 carbon atoms, more preferably from 12 to 22 carbon atoms, even more preferably from 14 to 22 carbon atoms and better still from 16 to 20 carbon atoms, and
X represents a cation chosen, for example, from the ions of alkali metals, such as Na, Li or K, preferably Na or K, the ions of alkaline earth metals, such as Mg, ammonium groups and their mixtures.

The acyl group can in particular be chosen from the lauroyl, myristoyl, behenoyl, palmitoyl, stearoyl, isostearoyl, olivoyl, cocoyl or oleoyl groups and their mixtures.

Preferably, R is a cocoyl group.

ii) Glycinates of following formula (II):

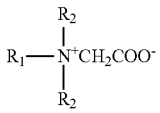

in which:
R$_1$ represents a saturated or unsaturated, linear or branched, hydrocarbon chain comprising from 10 to 30 carbon atoms, preferably from 12 to 22 carbon atoms and better still from 16 to 20 carbon atoms; R$_1$ is advantageously chosen from the lauryl, myristyl, palmityl, stearyl, cetyl, cetearyl or oleyl groups and their mixtures and preferably from the stearyl and oleyl groups, the R$_2$ groups, which are identical or different, represent an R"OH group, R" being an alkyl group comprising from 2 to 10 carbon atoms, preferably from 2 to 5 carbon atoms.

Mention may be made, as the compound of formula (I), for example, of the compounds carrying the INCI name sodium cocoyl glycinate, such as, for example, Amilite GCS-12, sold by Ajinomoto, or potassium cocoyl glycinate, such as, for example, Amilite GCK-12 from Ajinomoto.

Use may be made, as compounds of formula (II), of dihydroxyethyl oleyl glycinate or dihydroxyethyl stearyl glycinate.

Preferably, anionic surfactants are not soaps. So preferably anionic surfactants are chosen from synthetic anionic surfactants. More preferably, anionic surfactants are chosen from amino acid derivatives; alkyl sulfates; alkyl ether sulfates; olefin sulfonates and acylisethionates; and mixtures thereof. Even more preferably, anionic surfactants are chosen from amino acid derivatives, alkyl ether sulfates, and mixtures thereof.

It is preferable that the anionic surfactant be selected from the group consisting of: sodium laureth sulfate, ammonium laureth sulfate, disodium lauryl sulfosuccinate, disodium laureth sulfosuccinate, diammonium lauryl sulfosuccinate, diethylhexyl sodium sulfosuccinate, sodium oleyl succinate, sodium lauroyl methyl isethionate, sodium lauryl isethionate, sodium cocoyl isethionate, sodium laureth-5 carboxylate, lauryl ether carboxylic acid, ammonium lauryl sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, potassium lauryl sulfate, potassium laureth sulfate, ammonium cocoyl sulfate, ammonium lauroyl sulfate, sodium cocoyl sulfate, sodium lauroyl sulfate, potassium cocoyl sulfate, monoethanolamine cocoyl sulfate, sodium tridecyl benzene sulfonate, sodium dodecyl benzene sulfonate, sodium C$_{14-16}$ olefin sulfonate, sodium lauryl sarcosinate, sodium lauroyl sarcosinate, stearoyl sarcosine, lauryl sarcosine, cocoyl sarcosine, sodium methyl cocoyl taurate, sodium methyl lauroyl taurate, sodium lauroyl glutamate, sodium cocoyl glutamate, disodium cocoyl glutamate, potassium myristoyl glutamate, TEA-cocoyl glutamate, sodium cocoyl glycinate, potassium cocoyl glycinate, sodium cocoyl alaninate, TEA-cocoyl alaninate and mixtures thereof.

The amount of the anionic surfactant(s) in the composition according to the present invention may be 0.01% by weight or more, preferably 0.1% by weight or more, and more preferably 0.5% by weight or more relative to the total weight of the composition.

On the other hand, the amount of the anionic surfactant(s) in the composition according to the present invention may be 15% by weight or less, preferably 10% by weight or less, and more preferably 5% by weight or less relative to the total weight of the composition.

Thus, the amount of the anionic surfactant(s) in the composition according to the present invention may range from 0.01% to 15% by weight, preferably from 0.1% to 10% by weight, and more preferably from 0.5% to 5% by weight relative to the total weight of the composition.

(Polyglyceryl Fatty Acid Ester)

The composition according to the present invention comprises (d) at least one polyglyceryl fatty acid ester. A single type of polyglyceryl fatty acid ester may be used, but two or more different types of polyglyceryl fatty acid ester may be used in combination.

The polyglyceryl fatty acid ester can function as a non-ionic surfactant.

It is preferable that the polyglyceryl fatty acid ester have a polyglycerol moiety derived from 2 to 10 glycerols, more preferably from 2 to 8 glycerols, and further more preferably from 2 to 6 glycerols.

The polyglyceryl fatty acid ester may have an HLB (Hydrophilic Lipophilic Balance) value of from 7.0 to 16.0, preferably from 8.0 to 15.0, and more preferably from 10.0 to 13.0. If two or more polyglyceryl fatty acid esters are used, the HLB value is determined by the weight average of the HLB values of all the polyglyceryl fatty acid esters.

The polyglyceryl fatty acid ester may be chosen from the mono, di and tri esters of saturated or unsaturated acid, preferably saturated acid, including 4 to 30 carbon atoms, preferably 6 to 20 carbon atoms, and more preferably 8 to 16 carbon atoms, such as lauric acid, oleic acid, stearic acid, isostearic acid, capric acid, caprylic acid, and myristic acid.

The polyglyceryl fatty acid ester may be selected from the group consisting of PG2 caprylate, PG2 sesquicaprylate, PG2 dicaprylate, PG2 tricaprylate, PG2 caprate, PG2 sesquicaprate, PG2 dicaprate, PG2 tricaprate, PG2 laurate, PG2 sesquilaurate, PG2 dilaurate, PG2 trilaurate, PG2 myristate, PG2 sesquimyristate, PG2 dimyristate, PG2 trimyristate, PG2 stearate, PG2 sesquistearate, PG2 distearate, PG2 tristearate, PG2 isostearate, PG2 sesquiisostearate, PG2 diisostearate, PG2 triisostearate, PG2 oleate, PG2 sesquioleate, PG2 dioleate, PG2 trioleate, PG3 caprylate, PG3 sesquicaprylate, PG3 dicaprylate, PG3 tricaprylate, PG3 caprate, PG3 sesquicaprate, PG3 dicaprate, PG3 tricaprate, PG3 laurate, PG3 sesquilaurate, PG3 dilaurate, PG3 trilaurate, PG3 myristate, PG3 sesquimyristate, PG3 dimyristate, PG3 trimyristate, PG3 stearate, PG3 sesquistearate, PG3 distearate, PG3 tristearate, PG3 isostearate, PG3 sesquiisostearate, PG3 diisostearate, PG3 triisostearate, PG3 oleate, PG3 sesquioleate, PG3 dioleate, PG3 trioleate, PG4 caprylate, PG4 sesquicaprylate, PG4 dicaprylate, PG4 tricaprylate, PG4 caprate, PG4 sesquicaprate, PG4 dicaprate, PG4 tricaprate, PG4 laurate, PG4 sesquilaurate, PG4 dilaurate, PG4 trilaurate, PG4 myristate, PG4 sesquimyristate, PG4 dimyristate, PG4 trimyristate, PG4 stearate, PG4 sesquistearate, PG4 distearate, PG4 tristearate, PG4 isostearate, PG4 sesquiisostearate, PG4 diisostearate, PG4 triisostearate, PG4 oleate, PG4 sesquioleate, PG4 dioleate, PG4 trioleate, PG5 caprylate, PG5 sesquicaprylate, PG5 dicaprylate, PG5 tricaprylate, PG5 tetracaprylate, PG5 caprate, PG5 sesquicaprate, PG5 dicaprate, PG5 tricaprate, PG5 tetracaprate, PG5 laurate, PG5 sesquilaurate, PG5 dilaurate, PG5 trilaurate, PG5 tetralaurate, PG5 myristate, PG5 sesquimyristate, PG5 dimyristate, PG5 trimyristate, PG5 tetramyristate, PG5 stearate, PG5 sesquistearate, PG5 distearate, PG5 tristearate, PG5 tetrastearate, PG5 isostearate, PG5 sesquiisostearate, PG5 diisostearate, PG5 triisostearate, PG5 tetraisostearate, PG5 oleate, PG5 sesquioleate, PG5 dioleate, PG5 trioleate, PG5 tetraoleate, PG6 caprylate, PG6 sesquicaprylate, PG6 dicaprylate, PG6 tricaprylate, PG6 tetracaprylate, PG6 pentacaprylate, PG6 caprate, PG6 sesquicaprate, PG6 dicaprate, PG6 tricaprate, PG6 tetracaprate, PG6 pentacaprate, PG6 laurate, PG6 sesquilaurate, PG6 dilaurate, PG6 trilaurate, PG6 tetralaurate, PG6 pentalaurate, PG6 myristate, PG6 sesquimyristate, PG6 dimyristate, PG6 trimyristate, PG6 tetramyristate, PG6 pentamyristate, PG6 stearate, PG6 sesquistearate, PG6 distearate, PG6 tristearate, PG6 tetrastearate, PG6 pentastearate, PG6 isostearate, PG6 sesquiisostearate, PG6 diisostearate, PG6 triisostearate, PG6 tetraisostearate, PG6 pentaisostearate, PG6 oleate, PG6 sesquioleate, PG6 dioleate, PG6 trioleate, PG6 tetraoleate, PG6 pentaoleate, PG10 caprylate, PG10 sesquicaprylate, PG10 dicaprylate, PG10 tricaprylate, PG10 tetracaprylate, PG10 pentacaprylate, PG10 hexacaprylate, PG10 caprate, PG10 sesquicaprate, PG10 dicaprate, PG10 tricaprate, PG10 tetracaprate, PG10 pentacaprate, PG10 hexacaprate, PG10 laurate, PG10 sesquilaurate, PG10 dilaurate, PG10 trilaurate, PG10 tetralaurate, PG10 pentalaurate, PG10 hexalaurate, PG10 myristate, PG10 sesquimyristate, PG10 dimyristate, PG10 trimyristate, PG10 tetramyristate, PG10 pentamyristate, PG10 hexamyristate, PG10 stearate, PG10 sesquistearate, PG10 distearate, PG10 tristearate, PG10 tetrastearate, PG10 pentastearate, PG10 hexastearate, PG10 isostearate, PG10 sesquiisostearate, PG10 diisostearate, PG10 triisostearate, PG10 tetraisostearate, PG10 pentaisostearate, PG10 hexaisostearate, PG10 oleate, PG10 sesquioleate, PG10 dioleate, PG10 trioleate, PG10 tetraoleate, PG10 pentaoleate, and PG10 hexaoleate.

It is preferable that the polyglyceryl fatty acid ester be chosen from:
polyglyceryl dicaprate comprising 2 to 6 glycerol units,
polyglyceryl monolaurate comprising 2 to 6 glycerol units,
polyglyceryl mono(iso)stearate comprising 2 to 6 glycerol units,
polyglyceryl monooleate comprising 2 to 6 glycerol units, and
polyglyceryl dioleate comprising 2 to 6 glycerol units.

In one embodiment, the raw material of the polyglyceryl fatty acid ester may be chosen from a mixture of polyglyceryl fatty acid esters, preferably with a polyglyceryl moiety derived from 2 to 10 glycerins, more preferably 2 to 6 glycerins, wherein the mixture preferably comprises 30% by weight or more of a polyglyceryl fatty acid ester with a polyglyceryl moiety consisting of 2 to 6 glycerins.

It may be preferable than the raw material of the polyglyceryl fatty acid ester comprise esters of a fatty acid and polyglycerine containing 70% or more of polyglycerine whose polymerization degree is 2 or more, preferably esters of a fatty acid and polyglycerine containing equal to or more than 60% of polyglycerine whose polymerization degree is between 2 and 6, and more preferably esters of a fatty acid and polyglycerine containing equal to or more than 30% of polyglycerine whose polymerization degree is 2 to 6.

The amount of the polyglyceryl fatty acid ester(s) in the composition according to the present invention may be 0.1% by weight or more, preferably 1% by weight or more, and more preferably 5% by weight or more relative to the total weight of the composition.

On the other hand, the amount of the polyglyceryl fatty acid ester(s) in the composition according to the present invention may be 20% by weight or less, preferably 15% by weight or less, and more preferably 10% by weight or less relative to the total weight of the composition.

Thus, the amount of the polyglyceryl fatty acid ester(s) in the composition according to the present invention may range from 0.1% to 20% by weight, preferably from 1% to 15% by weight, and more preferably from 5% to 10% by weight relative to the total weight of the composition.

(Alkylpolyglycoside)

The composition according to the present invention comprises (e) at least one alkylpolyglycoside. A single type of alkylpolyglycoside may be used, but two or more different types of alkylpolyglycoside may be used in combination.

For the purposes of the present invention, the term "alkylpolyglycoside" is intended to mean an alkylmonosaccharide (degree of polymerization 1) or an alkylpolysaccharide (degree of polymerization greater than 1).

The alkylpolyglycoside can function as a nonionic surfactant.

The alkylpolyglycosides may be used alone or in the form of mixtures of several alkylpolyglycosides.

The surfactant of alkylpolyglycoside type may be selected from the compound of formula (I):

$$R(O)(G)_x \qquad (I)$$

in which the radical R is a linear or branched $C_{10}$-$C_{22}$ alkyl radical, preferably a $C_{10}$-$C_{20}$ alkyl radical, G is a saccharide residue and x ranges from 1 to 5, preferably from 1.05 to 2.5 and more preferentially from 1.1 to 2.

The saccharide residue may be chosen from the group of glucose, dextrose, saccharose, fructose, galactose, maltose, maltotriose, lactose, cellobiose, mannose, ribose, dextran, talose, allose, xylose, levoglucan, cellulose and starch. More preferentially, the saccharide residue denotes glucose.

It should also be noted that each unit of the polysaccharide part of the alkylpolyglycoside may be in α or β isomer form, in L or D form, and the configuration of the saccharide residue may be of furanoside or pyranoside type.

It is, of course, possible to use mixtures of alkylpolysaccharides, which may differ from each other in the nature of the borne alkyl unit and/or the nature of the bearing polysaccharide chain.

In addition, it is particularly advantageous, according to the present invention, to use together a fatty alcohol and an alkylpolyglycoside of which the alkyl part is identical to that of the selected fatty alcohol.

Fatty alcohol/alkylpolyglycoside emulsifying mixtures as defined are described in particular in patent applications WO 92/06778, WO 95/13863 and WO 98/47610.

Among the fatty alcohol/alkylpolyglycoside mixtures that are particularly preferred, mention may be made of the products sold by the company SEPPIC under the name Montanov®, such as the following mixtures:
cetylstearyl alcohol/cocoyl glucoside (Montanov 82®),
arachidyl alcohol and behenyl alcohol/arachidyl glucoside (Montanov 802®),
myristyl alcohol/myristyl glucoside (Montanov 14®),
cetylstearyl alcohol/cetylstearyl glucoside (Montanov 68®), $C_{14}$-$C_{22}$ alcohol/$C_{12}$-$C_{20}$ alkyl glucoside (Montanov L®), cocoyl alcohol/cocoyl glucoside (Montanov S®) and isostearyl alcohol/isostearyl glucoside (Montanov WO 18®).

According to one particular embodiment, the alkylpolyglycoside used in a composition according to the present invention is $C_{12}$-$C_{20}$ glucoside. It is advantageously used as a mixture with a $C_{14}$-$C_{22}$ alcohol.

According to one particular embodiment of the present invention, use is thus made of the $C_{14}$-$C_{22}$ alcohol/$C_{12}$-$C_{20}$ alkylglucoside mixture, such as the product sold by the company SEPPIC under the name Montanov 68®, consisting of approximately 20% of $C_{12}$-$C_{20}$ alkylglucoside and of approximately 80% of $C_{14}$-$C_{22}$ alcohol.

According to another embodiment, the alkylpolyglycoside used in a composition according to the present invention is $C_{10}$-$C_{20}$ glucoside, preferably $C_{10}$-$C_{15}$ glucoside, and more preferably $C_{10}$-$C_{12}$ glucoside. In particular, the use of decyl glucoside may be even more preferable.

The amount of the alkylpolyglycoside(s) in the composition according to the present invention may be 0.01% by weight or more, preferably 0.05% by weight or more, and more preferably 0.1% by weight or more relative to the total weight of the composition.

On the other hand, the amount of the alkylpolyglycoside(s) in the composition according to the present invention may be 15% by weight or less, preferably 10% by weight or less, and more preferably 5% by weight or less relative to the total weight of the composition.

Thus, the amount of the alkylpolyglycoside(s) in the composition according to the present invention may range from 0.01% to 15% by weight, preferably from 0.05% to 10% by weight, and more preferably from 0.1% to 5% by weight relative to the total weight of the composition.

(Polyol with 5 or More Carbon Atoms)

The composition according to the present invention may comprise (f) at least one polyol with 5 or more carbon atoms. A single type of such polyol may be used, but two or more different types of such polyol may be used in combination.

The polyol with 5 or more carbon atoms may be selected from diols with 5 or more carbon atoms, preferably $C_5$-$C_{10}$ diols, and more preferably pentyleleglycol, hexyleneglycol, and mixtures thereof.

Pentyleneglycol encompasses isomers thereof. Thus, pentyleneglycol may be 1,2-pentyleneglycol, 1,3-pentyleneglycol, 1,4-pentyleneglycol, 1,5-pentyleneglycol, 2,3-pentyleneglycol, and 2,4-penyleneglycol. 1,2-pentyleneglycol may be preferable.

Hexyleneglycol encompasses isomers thereof. Thus, hexyleneglycol may be 1,2-hexyleneglycol, 1,3-hexyleneglucol, 1,4-hexyleneglycol, 1,5-hexyleneglycol, 1,6-hexyleneglycol, 2,3-hexyleneglycol, 2,4-hexyleneglycol, 2,5-hexyleneglycol, and 2-methyl-2,4-pentanediol. 2-methyl-2,4-pentanediol may be preferable.

The amount of the polyol(s) with 5 or more carbon atoms in the composition according to the present invention may be 0.01% by weight or more, preferably 0.1% by weight or more, and more preferably 0.5% by weight or more relative to the total weight of the composition.

On the other hand, the amount of the polyol(s) with 5 or more carbon atoms in the composition according to the present invention may be 15% by weight or less, preferably 10% by weight or less, and more preferably 5% by weight or less relative to the total weight of the composition.

Thus, the amount of the polyol(s) with 5 or more carbon atoms in the composition according to the present invention may range from 0.01% to 15% by weight, preferably from 0.1% to 10% by weight, and more preferably from 0.5% to 5% by weight relative to the total weight of the composition.

(Water)

The composition according to the present invention may comprise water.

The amount of the water in the composition according to the present invention may be 50% by weight or more, preferably 60% by weight or more, and more preferably 70% by weight or more, relative to the total weight of the first composition.

The amount of the water in the composition according to the present invention may be 95% by weight or less, preferably 90% by weight or less, and more preferably 85% by weight or less, relative to the total weight of the first composition.

The amount of water in the composition according to the present invention may range from 50% to 95% by weight, preferably from 60% to 90% by weight, and more preferably from 70 to 85% by weight, relative to the total weight of the composition.

(Additional Oil)

The composition according to the present invention may comprise at least one additional oil other than (a) the ether oil. A single type of such additional oil may be used, but two or more different types of such additional oil may be used in combination.

The additional oil may be volatile or non-volatile.

The additional oil may be a non-polar oil such as a hydrocarbon oil, a silicone oil, or the like; a polar oil such as a plant or animal oil and an ester oil; or a mixture thereof.

The additional oil may be selected from the group consisting of oils of plant or animal origin, synthetic oils, silicone oils, hydrocarbon oils, and fatty alcohols.

As examples of plant oils, mention may be made of, for example, linseed oil, *camellia* oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate, and isostearyl neopentanoate.

Esters of $C_4$-$C_{22}$ dicarboxylic or tricarboxylic acids and of $C_1$-$C_{22}$ alcohols, and esters of monocarboxylic, dicarboxylic, or tricarboxylic acids and of non-sugar $C_4$-$C_{26}$ dihydroxy, trihydroxy, tetrahydroxy, or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides, or polysaccharides.

Examples of suitable sugars that may be mentioned include sucrose (or saccharose), glucose, galactose, ribose, fucose, maltose, fructose, mannose, arabinose, xylose, and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters, and polyesters, and mixtures thereof.

These esters may be, for example, oleates, laurates, palmitates, myristates, behenates, cocoates, stearates, linoleates, linolenates, caprates, and arachidonates, or mixtures thereof such as, especially, oleopalmitate, oleostearate, and palmitostearate mixed esters, as well as pentaerythrityl tetraethyl hexanoate.

More particularly, use is made of monoesters and diesters and especially sucrose, glucose, or methylglucose monooleates or dioleates, stearates, behenates, oleopalmitates, linoleates, linolenates, and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate), and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, the silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprise in their structure one or more organofunctional groups attached via a hydrocarbon-based group.

Organopolysiloxanes are defined in greater detail in Walter Noll's Chemistry and Technology of Silicones (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylalkylsiloxane, such as Silicone Volatile® FZ 3109 sold by the company Union Carbide, of the formula:

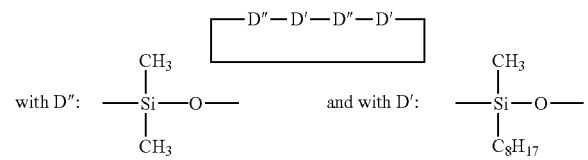

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane; and (ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, Volatile Silicone Fluids for Cosmetics. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm²/s; and the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

The phenyl silicone oil may be chosen from the phenyl silicones of the following formula:

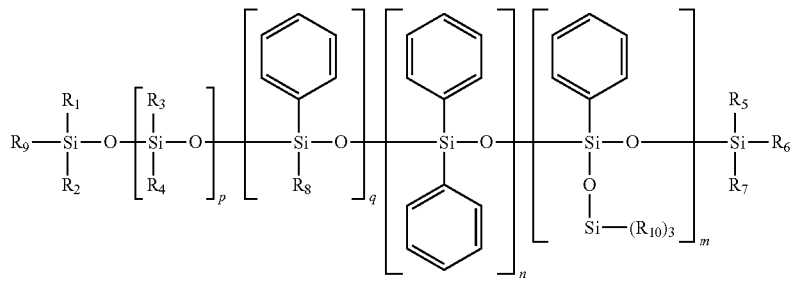

in which
- $R_1$ to $R_{10}$, independently of each other, are saturated or unsaturated, linear, cyclic or branched $C_1$-$C_{30}$ hydrocarbon-based radicals, preferably $C_1$-$C_{12}$ hydrocarbon-based radicals, and more preferably $C_1$-$C_6$ hydrocarbon-based radicals, in particular methyl, ethyl, propyl, or butyl radicals, and
- m, n, p, and q are, independently of each other, integers of 0 to 900 inclusive, preferably 0 to 500 inclusive, and more preferably 0 to 100 inclusive, with the proviso that the sum n+m+q is other than 0.

Examples that may be mentioned include the products sold under the following names:
- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- certain oils of the SF series from General Electric, such as SF 1023, SF 1154, SF 1250, and SF 1265.

As the phenyl silicone oil, phenyl trimethicone ($R_1$ to $R_{10}$ are methyl; p, q, and n=0; m=1 in the above formula) is preferable.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:
- linear or branched, optionally cyclic, $C_6$-$C_{16}$ lower alkanes. Examples that may be mentioned include hexane, undecane, dodecane, tridecane, and isoparaffins, for instance isohexadecane, isododecane, and isodecane; and
- linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that the fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from cetyl alcohol, octyldodecanol, hexyldecanol, and mixtures thereof.

It is also preferable that the additional oil be chosen from oils with a molecular weight below 600 g/mol.

It may be preferable that the additional oil be chosen from ester oils, silicone oils, and mixtures thereof.

The amount of the additional oil(s) in the composition according to the present invention may be 1% by weight or more, preferably 3% by weight or more, and more preferably 5% by weight or more, relative to the total weight of the composition.

The amount of the additional oil(s) in the composition according to the present invention may be 20% by weight or less, preferably 15% by weight or less, and more preferably 10% by weight or less, relative to the total weight of the composition.

The amount of the additional oil(s) in the composition according to the present invention may be from 1% to 20% by weight, preferably from 3% to 15% by weight, and more preferably from 5% to 10% by weight, relative to the total weight of the composition.

(Additional Surfactant)

The composition according to the present invention may comprise at least one additional surfactant other than the (b) amphoteric surfactant, the (c) anionic surfactant, the (d) polyglyceryl fatty acid ester, and the (e) alkylpolyglycoside. A single type of such additional surfactant may be used, but two or more different types of such additional surfactant may be used in combination.

The additional surfactant may be selected from cationic surfactants and nonionic surfactants other than the (d) polyglyceryl fatty acid ester, and the (e) alkylpolyglycoside.

Cationic Surfactant

The cationic surfactant may be selected from the group consisting of optionally polyoxyalkylenated, primary, secondary or tertiary fatty amine salts, quaternary ammonium salts, and mixtures thereof.

Examples of quaternary ammonium salts that may be mentioned include, but are not limited to:

those of general formula (V) below:

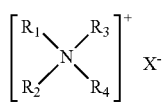

wherein $R_1$, $R_2$, $R_3$, and $R_4$, which may be identical or different, are chosen from linear and branched aliphatic radicals comprising from 1 to 30 carbon atoms and optionally comprising heteroatoms such as oxygen, nitrogen, sulfur and halogens. The aliphatic radicals may be chosen, for example, from alkyl, alkoxy, $C_2$-$C_6$ polyoxyalkylene, alkylamide, $(C_{12}$-$C_{22})$alkylamido$(C_2$-$C_6)$alkyl, $(C_{12}$-$C_{22})$alkylacetate and hydroxyalkyl radicals; and aromatic radicals such as aryl and alkylaryl; and $X^-$ is chosen from halides, phosphates, acetates, lactates, $(C_2$-$C_6)$ alkyl sulfates and alkyl- or alkylaryl-sulfonates; quaternary ammonium salts of imidazoline, for instance those of formula (VI) below:

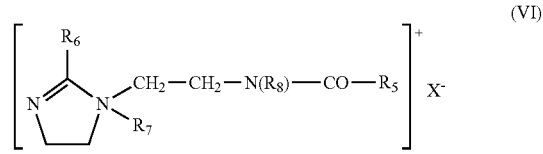

wherein:

$R_5$ is chosen from alkenyl and alkyl radicals comprising from 8 to 30 carbon atoms, for example fatty acid derivatives of tallow or of coconut;

$R_6$ is chosen from hydrogen, $C_1$-$C_4$ alkyl radicals, and alkenyl and alkyl radicals comprising from 8 to 30 carbon atoms;

$R_7$ is chosen from $C_1$-$C_4$ alkyl radicals;

$R_8$ is chosen from hydrogen and $C_1$-$C_4$ alkyl radicals; and $X^-$ is chosen from halides, phosphates, acetates, lactates, alkyl sulfates, alkyl sulfonates, and alkylaryl sulfonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Examples of such products include, but are not limited to, Quaternium-27 (CTFA 1997) and Quaternium-83 (CTFA 1997), which are sold under the names "Rewoquat®" W75, W90, W75PG and W75HPG by the company Witco;

diquaternary ammonium salts of formula (VII):

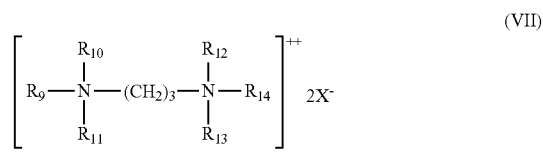

wherein:

$R_9$ is chosen from aliphatic radicals comprising from 16 to 30 carbon atoms;

$R_{10}$, $R_{11}$, $R_{12}$, $R_{13}$, and $R_{14}$, which may be identical or different, are chosen from hydrogen and alkyl radicals comprising from 1 to 4 carbon atoms; and $X^-$ is chosen from halides, acetates, phosphates, nitrates, ethyl sulfates, and methyl sulfates.

An example of one such diquaternary ammonium salt is propanetallowdiammonium dichloride; and quaternary ammonium salts comprising at least one ester function, such as those of formula (VIII) below:

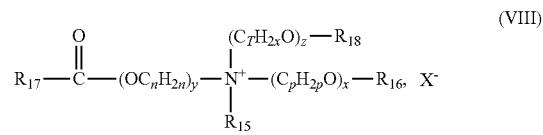

wherein:

$R_{15}$ is chosen from $C_1$-$C_6$ alkyl radicals and $C_1$-$C_6$ hydroxyalkyl and dihydroxyalkyl radicals;

$R_{16}$ is chosen from:

the radical below:

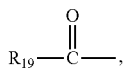

linear and branched, saturated and unsaturated $C_1$-$C_{22}$ hydrocarbon-based radicals $R_{20}$, and hydrogen, $R_{18}$ is chosen from:

the radical below:

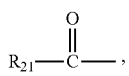

linear and branched, saturated and unsaturated $C_1$-$C_6$ hydrocarbon-based radicals Rn, and hydrogen, $R_{17}$, $R_{19}$, and Rei, which may be identical or different, are chosen from linear and branched, saturated and unsaturated, $C_7$-$C_{21}$, hydrocarbon-based radicals;

r, n, and p, which may be identical or different, are chosen from integers ranging from 2 to 6;

y is chosen from integers ranging from 1 to 10;

x and z, which may be identical or different, are chosen from integers ranging from 0 to 10;

$X^-$ is chosen from simple and complex, organic and inorganic anions; with the proviso that the sum x+y+z ranges from 1 to 15, that when x is 0, $R_{16}$ denotes $R_{20}$, and that when z is 0, $R_{18}$ denotes $R_{11}$. $R_{15}$ may be chosen from linear and branched alkyl radicals. In one embodiment, $R_{15}$ is chosen from linear alkyl radicals. In another embodiment, $R_{15}$ is chosen from methyl, ethyl, hydroxyethyl, and dihydroxypropyl radicals, for example methyl and ethyl radicals. In one embodiment, the sum x+y+z ranges from 1 to 10. When $R_{16}$ is a hydrocarbon-based radical $R_{20}$, it may be long and comprise from 12 to 22 carbon atoms, or short and comprise from 1 to 3 carbon atoms. When $R_{18}$ is a hydrocarbon-based radical $R_{22}$, it may comprise, for example, from 1 to 3 carbon atoms. By way of a non-limiting example, in one embodiment, $R_{17}$, $R_{19}$, and $R_{21}$, which may be identical or different, are chosen from linear and branched, saturated and unsaturated, $C_{11}$-$C_{21}$ hydrocarbon-based radicals, for example from linear and branched, saturated and unsaturated $C_{11}$-$C_{21}$ alkyl and alkenyl radicals. In another embodiment, x and z, which may be identical or different, are 0 or 1. In one embodiment, y is equal to 1. In another embodiment, r, n and p, which may be identical or different, are equal to 2 or 3, for example equal to 2. The anion $X^-$ may be chosen from, for example, halides, such as chloride, bromide, and iodide; and $C_1$-$C_4$ alkyl sulfates, such as methyl sulfate. However, methanesulfonate, phosphate, nitrate, tosylate, an anion derived from an organic acid, such as acetate and lactate, and any other anion that is compatible with the ammonium comprising an ester function, are other non-limiting examples of anions that may be used according to the invention. In one embodiment, the anion $X^-$ is chosen from chloride and methyl sulfate.

In another embodiment, the ammonium salts of formula (VIII) may be used, wherein:

$R_{15}$ is chosen from methyl and ethyl radicals, x and y are equal to 1;

z is equal to 0 or 1;

r, n and p are equal to 2;

$R_{16}$ is chosen from:

the radical below:

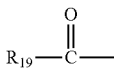

methyl, ethyl, and $C_{14}$-$C_{22}$ hydrocarbon-based radicals, hydrogen;

$R_{18}$ is chosen from:

the radical below:

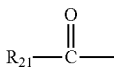

hydrogen;

$R_{17}$, $R_{19}$, and $R_{21}$, which may be identical or different, are chosen from linear and branched, saturated and unsaturated, $C_{13}$-$C_{17}$ hydrocarbon-based radicals, for example from linear and branched, saturated and unsaturated, $C_{13}$-$C_{17}$ alkyl and alkenyl radicals.

In one embodiment, the hydrocarbon-based radicals are linear.

Non-limiting examples of compounds of formula (VIII) that may be mentioned include salts, for example chloride and methyl sulfate, of diacyloxyethyl-dimethylammonium, of diacyloxyethyl-hydroxyethyl-methylamm-onium, of monoacyloxyethyl-dihydroxyethyl-methylammonium, of triacyloxyethyl-methylammonium, of monoacyloxyethyl-hydroxyethyl-dimethyl-ammonium, and mixtures thereof. In one embodiment, the acyl radicals may comprise from 14 to 18 carbon atoms, and may be derived, for example, from a plant oil, for instance palm oil and sunflower oil. When the compound comprises several acyl radicals, these radicals may be identical or different.

These products may be obtained, for example, by direct esterification of optionally oxyalkylenated triethanolamine, triisopropanolamine, alkyldiethanolamine or alkyldiisopropanolamine onto fatty acids or onto mixtures of fatty acids of plant or animal origin, or by transesterification of the methyl esters thereof. This esterification may be followed by a quaternization using an alkylating agent chosen from alkyl halides, for example methyl and ethyl halides; dialkyl sulfates, for example dimethyl and diethyl sulfates; methyl methanesulfonate; methyl para-toluenesulfonate; glycol chlorohydrin; and glycerol chlorohydrin.

Such compounds are sold, for example, under the names Dehyquart® by the company Cognis, Stepanquat® by the company Stepan, Noxamium® by the company Ceca, and "Rewoquat® WE 18" by the company Rewo-Goldschmidt.

The compositions according to the invention may comprise, for example, a mixture of quaternary ammonium mono-, di- and triester salts with a weight majority of diester salts.

A non-limiting example of a mixture of ammonium salts that may be used in the compositions according to the invention is that comprising from 15% to 30% by weight of acyloxyethyl-dihydroxyethyl-methylammonium methyl sulfate, from 45% to 60% by weight of diacyloxyethyl-hydroxyethyl-methylammonium methyl sulfate, and from 15% to 30% by weight of triacyloxyethyl-methylammonium methyl sulfate, the acyl radicals of all these compounds comprising from 14 to 18 carbon atoms and being derived from optionally partially hydrogenated palm oil.

Other non-limiting examples of ammonium salts that may be used in the compositions according to the invention include the ammonium salts comprising at least one ester function described in U.S. Pat. Nos. 4,874,554 and 4,137,180.

Among the quaternary ammonium salts mentioned above that may be used in compositions according to the invention include, but are not limited to, those corresponding to formula (V), for example tetraalkylammonium chlorides, for instance dialkyldimethylammonium and alkyltrimethylammonium chlorides in which the alkyl radical comprises from about 12 to 22 carbon atoms, such as behenyltrimethylammonium, distearyldimethylammonium, cetyltrimethylammonium and benzyldimethylstearylammonium chloride; palmitylamidopropyltrimethylammonium chloride; and stearamidopropyldimethyl(myristyl acetate)ammonium chloride, sold under the name "Ceraphyl® 70" by the company Van Dyk.

According to one embodiment, the at least one cationic surfactant that may be used in the compositions of the invention is chosen from quaternary ammonium salts, for example from behenyltrimethylammonium chloride, cetyltrimethylammonium chloride (cetrimonium chloride), Quaternium-83, Quaternium-87, Quaternium-22, behenylamidopropyl-2,3-dihydroxypropyldimethylammonium chloride, palmitylamidopropyltrimethylammonium chloride, and stearamidopropyldimethylamine.

Nonionic Surfactant

The nonionic surfactants are compounds well known in and of themselves (see, e.g., in this regard, "Handbook of Surfactants" by M. R. Porter, Blackie & Son publishers (Glasgow and London), 1991, pp. 116-178).

Thus, they can, for example, be chosen from alcohols, alpha-diols, alkylphenols and esters of fatty acids, these compounds being ethoxylated, propoxylated or glycerolated and having at least one fatty chain comprising, for example, from 8 to 30 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils of plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives; amine oxides such as ($C_{10}$-$C_{14}$)alkylamine oxides or N—($C_{10}$-$C_{14}$)acylaminopropylmorpholine oxides; silicone surfactants; and mixtures thereof.

The nonionic surfactants may preferably be chosen from monooxyalkylenated, polyoxyalkylenated, monoglycerolated or polyglycerolated nonionic surfactants. The oxyalkylene units are more particularly oxyethylene or oxypropylene units, or a combination thereof, and are preferably oxyethylene units.

Examples of monooxyalkylenated or polyoxyalkylenated nonionic surfactants that may be mentioned include:
monooxyalkylenated or polyoxyalkylenated ($C_8$-$C_{24}$)alkylphenols,
saturated or unsaturated, linear or branched, monooxyalkylenated or polyoxyalkylenated $C_8$-$C_{30}$ alcohols,
saturated or unsaturated, linear or branched, monooxyalkylenated or polyoxyalkylenated $C_8$-$C_{30}$ amides,
esters of saturated or unsaturated, linear or branched, $C_8$-$C_{30}$ acids and of polyalkylene glycols,
monooxyalkylenated or polyoxyalkylenated esters of saturated or unsaturated, linear or branched, $C_8$-$C_{30}$ acids and of sorbitol,
saturated or unsaturated, monooxyalkylenated or polyoxyalkylenated plant oils, condensates of ethylene oxide and/or of propylene oxide, inter alia, alone or as mixtures.

The surfactants preferably contain a number of moles of ethylene oxide and/or of propylene oxide of between 1 and 100 and most preferably between 2 and 50. Advantageously, the nonionic surfactants do not comprise any oxypropylene units.

According to one of the embodiments of the present invention, the polyoxyalkylenated nonionic surfactants are chosen from polyoxyethylenated fatty alcohol (polyethylene glycol ether of fatty alcohol) and polyoxyethylenated fatty ester (polyethylene glycol ester of fatty acid).

Examples of polyoxyethylenated fatty alcohol (or $C_8$-$C_{30}$ alcohols) that may be mentioned include the adducts of ethylene oxide with lauryl alcohol, especially those containing from 9 to 50 oxyethylene units and more particularly those containing from 10 to 12 oxyethylene units (Laureth-10 to Laureth-12, as the CTFA names); the adducts of ethylene oxide with behenyl alcohol, especially those containing from 9 to 50 oxyethylene units (Beheneth-9 to Beheneth-50, as the CTFA names); the adducts of ethylene oxide with cetearyl alcohol (mixture of cetyl alcohol and stearyl alcohol), especially those containing from 10 to 30 oxyethylene units (Ceteareth-10 to Ceteareth-30, as the CTFA names); the adducts of ethylene oxide with cetyl alcohol, especially those containing from 10 to 30 oxyethylene units (Ceteth-10 to Ceteth-30, as the CTFA names); the adducts of ethylene oxide with stearyl alcohol, especially those containing from 10 to 30 oxyethylene units (Steareth-10 to Steareth-30, as the CTFA names); the adducts of ethylene oxide with isostearyl alcohol, especially those containing from 10 to 50 oxyethylene units (Isosteareth-10 to Isosteareth-50, as the CTFA names); and mixtures thereof.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

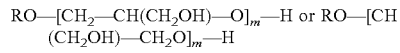

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is preferable to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

Examples of polyoxyethylenated fatty esters that may be mentioned include the adducts of ethylene oxide with esters of lauric acid, palmitic acid, stearic acid or behenic acid, and mixtures thereof, especially those containing from 9 to 100 oxyethylene units, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

According to one of the embodiments according to the present invention, the nonionic surfactant may be selected from esters of polyols with fatty acids with a saturated or unsaturated chain containing for example from 8 to 24 carbon atoms, preferably 12 to 22 carbon atoms, and polyoxyalkylenated derivatives thereof, preferably containing from 10 to 200, and more preferably from 10 to 100 oxyalkylene units, such as glyceryl esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sorbitol esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sugar (sucrose, maltose, glucose, fructose, and/or alkylglycose) esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; ethers of fatty alcohols; and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can be cited, and as polyoxyalkylenated derivatives thereof, mono-, di- or triester of fatty acids with a polyoxyalkylenated glycerol (mono-, di- or triester of fatty acids with a polyalkylene glycol ether of glycerol), preferably polyoxyethylenated glyceryl stearate (mono-, di- and/or tristearate), such as PEG-20 glyceryl stearate (mono-, di- and/or tristearate) can be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEGIN by Goldschmidt (CTFA name: glyceryl stearate SE), can also be used.

The sorbitol esters of $C_8$-$C_{24}$ fatty acids and polyoxyalkylenated derivatives thereof can be selected from sorbitan palmitate, sorbitan isostearate, sorbitan trioleate and esters of fatty acids and alkoxylated sorbitan containing for example from 20 to 100 EO, such as for example sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65, polyethylene sorbitan trioleate (polysorbate 85) or the compounds marketed under the trade names Tween 20 or Tween 60 by Uniqema.

As esters of fatty acids and glucose or alkylglucose, glucose palmitate, alkylglucose sesquistearates such as methylglucose sesquistearate, alkylglucose palmitates such as methylglucose or ethylglucose palmitate, methylglucoside fatty esters, the diester of methylglucoside and oleic acid (CTFA name: Methyl glucose dioleate), the mixed ester of methylglucoside and the mixture of oleic acid/hydroxystearic acid (CTFA name: Methyl glucose dioleate/hydroxystearate), the ester of methylglucoside and isostearic acid (CTFA name: Methyl glucose isostearate), the ester of methylglucoside and lauric acid (CTFA name: Methyl glucose laurate), the mixture of monoester and diester of methylglucoside and isostearic acid (CTFA name: Methyl glucose sesqui-isostearate), the mixture of monoester and diester of methylglucoside and stearic acid (CTFA name: Methyl glucose sesquistearate) and in particular the product marketed under the name Glucate SS by AMERCHOL, and mixtures thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (CTFA name: PEG-20 methyl glucose distearate) such as the product marketed under the name Glucam E-20 distearate by AMERCHOL, the polyethylene glycol ether of the mixture of monoester and diester of methyl-glucose and stearic acid with about 20 moles of ethylene oxide (CTFA name: PEG-20 methyl glucose sesquistearate) and in particular the product marketed under the name Glucamate SSE-20 by AMERCHOL and that marketed under the name Grillocose PSE-20 by GOLD-SCHMIDT, and mixtures thereof, can for example be cited.

As sucrose esters, saccharose palmito-stearate, saccharose stearate and saccharose monolaurate can for example be cited.

Mixtures of glycerides of alkoxylated plant oils such as mixtures of ethoxylated (200 EO) palm and copra (7 EO) glycerides can also be cited.

The nonionic surfactant according to the present invention preferably contains alkenyl or branched $C_{12}$-$C_{22}$ acyl chain such as oleyl or isostearyl group. More preferably, the nonionic surfactant according to the present invention is PEG-20 glyceryl triisostearate.

According to one of the embodiments according to the present invention, the nonionic surfactant may be selected from copolymers of ethylene oxide and of propylene oxide, in particular copolymers of the following formula:

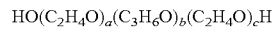

in which a, b and c are integers such that a+c ranges from 2 to 100 and b ranges from 14 to 60, and mixtures thereof.

According to one of the embodiments according to the present invention, the nonionic surfactant may be selected from silicone surfactants. Non-limiting mention may be made of those disclosed in documents U.S. Pat. Nos. 5,364,633 and 5,411,744.

The silicone surfactant may preferably be a compound of formula (I):

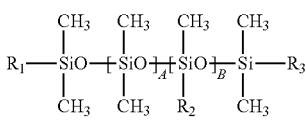

in which:
- $R_1$, $R_2$ and $R_3$, independently of each other, represent a $C_1$-$C_6$ alkyl radical or a radical $-(CH_2)_x-(OCH_2CH_2)_3$, $(OCH_2CH_2CH_2)_z-OR_4$, at least one radical $R_1$, $R_2$ or $R_3$ not being an alkyl radical; $R_4$ being a hydrogen, an alkyl radical or an acyl radical;
- A is an integer ranging from 0 to 200;
- B is an integer ranging from 0 to 50; with the proviso that A and B are not simultaneously equal to zero;
- x is an integer ranging from 1 to 6;
- y is an integer ranging from 1 to 30;
- z is an integer ranging from 0 to 5.

According to one preferred embodiment of the present invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

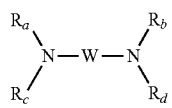

in which A is an integer ranging from 20 to 105, B is an integer ranging from 2 to 10 and y is an integer ranging from 10 to 20.

As examples of silicone surfactants of formula (I), mention may also be made of the compounds of formula (III):

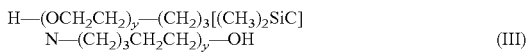

in which A' and y are integers ranging from 10 to 20.

Compounds of the present invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; A is 27, B is 3 and y is 12.

The compound Q4-3667 is a compound of formula (III) in which A is 15 and y is 13.

The HLB of the nonionic surfactant(s) may preferably be from 8 to 13, more preferably 9 to 12, and even more preferably 10 to 11. If two or more nonionic surfactants are used, the HLB value is determined by the weight average of the HLB values of all the nonionic surfactants. The HLB is the ratio between the hydrophilic part and the lipophilic part in the molecule. This term HLB is well known to those skilled in the art and is described in "The HLB system. A time-saving guide to emulsifier selection" (published by ICI Americas Inc., 1984). If the HLB of the nonionic surfactant(s) is lower than 8, the oily feeling after rinsing-off may remain. If the HLB of the nonionic surfactant(s) is higher than 13, the removability of the composition may be worse.

As the use of additional surfactant may cause dry feeling after use, it may be referable that the amount of the additional surfactant be limited.

The amount of the additional surfactant(s) in the composition according to the present invention may be 20% by weight or less, preferably 15% by weight or less, and more preferably 10% by weight or less, relative to the total weight of the composition.

The amount of the additional surfactant(s) in the composition according to the present invention may be from 1% to 20% by weight, preferably from 3% to 15% by weight, and more preferably from 5% to 10% by weight, relative to the total weight of the composition.

(Additional Polyol)

The composition according to the present invention may comprise at least one additional polyol other than the (f) polyol with 5 or more carbon atoms. A single type of such additional polyol may be used, but two or more different types of such additional polyol may be used in combination.

The term "polyol" here means an alcohol having two or more hydroxy groups, and does not encompass a saccharide or a derivative thereof. The derivative of a saccharide includes a sugar alcohol which is obtained by reducing one or more carbonyl groups of a saccharide, as well as a saccharide or a sugar alcohol in which the hydrogen atom or atoms in one or more hydroxy groups thereof has or have been replaced with at least one substituent such as an alkyl group, a hydroxyalkyl group, an alkoxy group, an acylgroup or a carbonyl group.

The polyol may be a $C_2$-$C_4$ polyol, preferably a $C_2$-$C_4$ polyol, comprising at least 2 hydroxy groups, and preferably 2 to 5 hydroxy groups.

The polyol may be a natural or synthetic polyol. The polyol may have a linear, branched or cyclic molecular structure.

The polyol may be selected from glycerins and derivatives thereof, and glycols and derivatives thereof. The polyol may be selected from the group consisting of glycerin, ethyleneglycol, propyleneglycol, and butyleneglycol.

As the use of additional polyol may cause instability and/or eye discomfort, it may be preferable that the amount of the additional polyol be limited.

The amount of the additional polyol(s) in the composition according to the present invention may be 20% by weight or less, preferably 15% by weight or less, and more preferably 10% by weight or less, relative to the total weight of the composition.

The amount of the additional polyol(s) in the composition according to the present invention may be from 1% to 20% by weight, preferably from 3% to 15% by weight, and more preferably from 5% to 10% by weight, relative to the total weight of the composition.

It is preferable that the composition according to the present invention includes no glycerin or butyleneglycol.

(Other Optional Ingredients)

The composition according to the present invention may contain one or more monoalcohols which are in the form of a liquid at room temperature (25° C.), such as for example linear or branched monoalcohols comprising from 1 to 6 carbon atoms, such as ethanol, propanol, butanol, isopropanol, isobutanol, pentanol, and hexanol.

The composition according to the present invention may preferably be acidic, neutral or slightly basic. Therefore, it may be preferable that the pH of the composition according to the present invention be from 4.0 to 8.0, more preferably from 4.5 to 7.0, and even more preferably from 4.8 to 6.0.

Among the acidifying agents, mention may be made, by way of example, of mineral or organic acids such as hydrochloric acid, ortho-phosphoric acid, sulfuric acid, carboxylic acids such as acetic acid, tartaric acid, citric acid, and lactic acid, and sulfonic acids.

Among the basifying agents, mention may be made, by way of example, of ammonium hydroxide, alkali metal carbonates, alkanolamines such as mono-, di- and triethanolamines and also their derivatives, sodium or potassium hydroxide and compounds of the formula below:

The composition according to the present invention may preferably be transparent or translucent, and more preferably transparent.

Also, the composition according to the present invention may preferably be gelled, and therefore, it can exhibit very good stability when, for example, being stored.

The composition according to the present invention may be a cosmetic composition, preferably a cleansing cosmetic composition, and more preferably a cleansing cosmetic composition for make-up products such as mascaras.

TABLE 1

| | Ingredients | Ex. 1 | Ex. 2 | Ex. 3 | Ex. 4 | Ex. 5 | Ex. 6 | Ex. 7 |
|---|---|---|---|---|---|---|---|---|
| Oil | (a) Dicaprylyl Ether | 7.5 | 7.5 | 7.5 | 7.5 | 7.5 | 7.5 | 7.5 |
| Amphoteric Surfactant | (b) Coco-Betaine | 6.0 | 6.0 | — | 6.0 | 6.0 | 6.0 | 6.0 |
| | (b) Cocamidopropyl Betaine | — | — | 6.0 | — | — | — | — |
| Anionic Surfactant | (c) Disodium Cocoyl Glutamate (and) Sodium Cocoyl Glutamate* | 0.75 | 0.75 | 0.75 | 0.75 | 0.75 | — | — |
| | (c) Sodium Cocoyl Glycinate | 0.18 | 0.18 | 0.18 | 0.18 | 0.18 | — | — |
| | (c) Sodium Lauroyl Sarcosinate | — | — | — | — | — | 0.93 | — |
| | (c) Sodium Laureth Sulfate | — | — | — | — | — | — | 0.93 |
| Nonionic Surfactant | (d) Polyglyceryl-6 Dicaprate | 7.56 | 7.80 | 7.80 | 8.73 | 8.55 | 7.80 | 7.80 |
| | (e) Decyl Glucoside | 4.44 | 4.20 | 4.20 | 0.27 | 0.45 | 4.20 | 4.20 |
| pH Adjuster | Citric Acid | 0.445 | 0.440 | 0.440 | 0.098 | 0.328 | 0.440 | 0.440 |
| Chelating Agent | Phytic Acid | — | — | — | 0.075 | — | — | — |
| Polyol | (f) Pentylene Glycol | — | — | — | 1.00 | — | — | — |
| Preservative/ Co-Preservative | Hydroxyacetophenone | 0.3 | 0.3 | 0.3 | — | 0.5 | 0.3 | 0.3 |
| | Phenoxyethanol | 0.3 | 0.3 | 0.3 | — | 0.2 | 0.3 | 0.3 |
| | Salicylic Acid | — | — | — | 0.198 | — | — | — |
| | Caprylyl Glycol | — | — | — | 0.200 | — | — | — |
| | Chlorphenesin | 0.1 | 0.1 | 0.1 | — | — | 0.1 | 0.1 |
| Water | Water | qsp 100 | qsp 100 | qsp 100 | qsp 100 | qsp 100 | qsp 100 | qsp 100 |

*Disodium Cocoyl Glutamate:Sodium Cocoyl Glutamate = 4:1 wherein

W denotes an alkylene such as propylene optionally substituted by a hydroxyl or a $C_1$-$C_4$ alkyl radical, and $R_a$, $R_b$, $R_c$ and $R_d$ independently denote a hydrogen atom, an alkyl radical or a $C_1$-$C_4$ hydroxyalkyl radical, which may be exemplified by 1,3-propanediamine and derivatives thereof.

The acidifying or basifying agent may be used in an amount ranging from 0.001% to 5% by weight, preferably from 0.01% to 3% by weight, and more preferably from 0.1% to 1% by weight, relative to the total weight of the composition according to the present invention.

The composition according to the present invention may also include various adjuvants conventionally used in compositions for cleansing, such as anionic, non-ionic, cationic, and amphoteric or zwitterionic polymers, antioxidants, chelating agents, sequestering agents, fragrances, dispersing agents, conditioning agents, film-forming agents, preservatives, co-preservatives, and mixtures thereof.

[Preparation]

The composition according to the present invention can be prepared by mixing the ingredients (a) to (e), as essential ingredients, as well as optional ingredient(s), as explained above.

The method and means to mix the above essential and optional ingredients are not limited. Any conventional method and means can be used to mix the above essential and optional ingredients to prepare the composition according to the present invention.

[Form]

The form of the composition according to the present invention is not particularly limited, and may take various forms such as an emulsion (O/W or W/O form), an aqueous gel, an aqueous solution, or the like. It is preferable that the composition according to the present invention be in the form of an O/W emulsion.

The compositions according to the present invention can be packaged for example in a jar, in a tube, in a pump-dispenser bottle, in a former or in an aerosol device that is customary in the cosmetics industry.

The compositions according to the present invention can, when they are intended to be packaged in an aerosol device, contain one or more propellant gases.

The invention also relates to a cosmetic product, preferably a cleansing cosmetic product, and more preferably a cleansing cosmetic product for make-up products such as mascaras, capable of forming a volume-expanded composition, comprising:

the composition according to the present invention; and a volume-expanded composition dispenser, for delivering said composition in the form of a volume-expanded composition.

The dispenser may be a bottle of former type or an aerosol device. The dispensers of former type typically comprise a container for containing a composition and a dispensing head for delivering the composition. The form can be formed by forcing the composition to pass through a material comprising a porous substance such as a sintered material, a filtering grid made of plastic or of metal, or similar structures. The container typically comprises either a squeezable wall or a pump and a dip tube for transferring the composition from the container into the head in order to deliver the product.

[Cosmetic Process]

The composition according to the present invention can be used for removing make-up and/or cleansing a keratin substance such as skin, including scalp, hair, eyelashes, and mucous membranes such as lips, preferably skin, lips and eyelashes, and in particular facial skin, lips and eyelashes.

Thus, the present invention also relates to a cosmetic process for cleansing a keratin substance, preferably skin, lips and eyelashes, comprising the step of applying the composition according to the present invention to the keratin substance. The application may be carried out in the form of a form. Thus, the composition according to the present invention may be in the form of a form, when being applied onto the keratin substance.

The present invention also relates to the use of the composition according to the present invention for cleansing a keratin substance such as skin, lips and eyelashes or removing make-up from the keratin substance.

EXAMPLES

The present invention will be described in a more detailed manner by way of examples.

However, these examples should not be construed as limiting the scope of the present invention.

[Compositions]

Each of cosmetic cleansing compositions according to Examples 1-7 (Ex. 1 to Ex. 7) in Table 1 and Comparative Examples 1-10 (Comp. Ex. 1 to Comp. Ex. 10) in Table 2 was prepared by mixing the ingredients shown in Tables 1 and 2. The numerical values for the amounts of the ingredients are all based on "% by weight" as active raw materials.

(Form)

A form was made for each of the compositions according to Examples 1-7 and Comparative Examples 6 and 10 by using a pump former dispenser (UF80-42: Autofoam Pump+ TG 42 150 ml bottle by APOLLO Industry Co., Ltd.). The formed form was put on the palm of 5 panelists. The form was evaluated in terms of density (A), elasticity (B) and lasting (C), in accordance with the following scoring system.

A: Density (5: High density to 1: Low density)
B: Elasticity (5: Elastic to 1: Not elastic at all)
C: Form Lasting (5: Last long to 1: Break quickly)

The scores were averaged, and further categorized by the following global criteria.

5: Very Good
4: Good
3: Fair
2: Poor
1: Very Poor

The results are shown in Tables 3 and 4.

(Removability of Water-Proof Mascara)

50 mg of a water-proof mascara (Magnum Push Up WP Mascara, Maybelline NY) was put onto 2.5 cm×2.5 cm of the forearm of 5 panelists, and dried fully. Next, each of the compositions according to Examples 1-7 and Comparative

TABLE 2

| | Ingredients | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 |
|---|---|---|---|---|---|---|---|---|---|---|---|
| Oil | (a) Dicaprylyl Ether | 7.5 | 7.5 | — | — | 7.5 | — | 7.5 | 7.5 | 7.5 | 7.5 |
| | Isopropyl Myristate | — | — | 7.5 | — | — | — | — | — | — | — |
| | Ethylhexyl Palmitate | — | — | — | 7.5 | — | — | — | — | — | — |
| Amphoteric Surfactant | (b) Coco-Betaine | — | — | 6.0 | 6.0 | 6.0 | 6.0 | 6.0 | 6.0 | 6.0 | — |
| | Lauryl Hydroxysultaine (and) Sodium Chloride | 6.0 | — | — | — | — | — | — | — | — | — |
| | Sodium Cocoamphoacetate | — | 6.0 | — | — | — | — | — | — | — | — |
| Anionic Surfactant | (c) Disodium Cocoyl Glutamate (and) Sodium Cocoyl Glutamate* | 0.75 | 0.75 | 0.75 | 0.75 | 0.75 | 0.75 | 0.75 | 0.75 | — | 0.75 |
| | (c) Sodium Cocoyl Glycinate | 0.18 | 0.18 | 0.18 | 0.18 | 0.18 | 0.18 | 0.18 | 0.18 | — | 0.18 |
| Nonionic Surfactant | (d) Polyglyceryl-6 Dicaprate | 7.80 | 7.80 | 7.80 | 7.80 | — | 7.56 | — | 7.56 | 7.56 | 7.56 |
| | PEG-6 Caprylic/Capric Glycerides | — | — | — | — | 4 | — | — | — | — | — |
| | Polysorbate 85 | — | — | — | — | 8 | — | — | — | — | — |
| | (e) Decyl Glucoside | 4.20 | 4.20 | 4.20 | 4.20 | — | 4.40 | 4.40 | — | 4.40 | 4.40 |
| pH Adjuster | Citric Acid | 0.440 | 0.435 | 0.430 | 0.430 | 0.440 | 0.445 | 0.445 | 0.250 | 0.445 | 0.445 |
| Chelating Agent | Phytic Acid | — | — | — | — | — | — | — | — | — | — |
| Polyol | (f) Pentylene Glycol | — | — | — | — | — | — | — | — | — | — |
| Preservative/ Co-Preservative | Hydroxyacetophenone | 0.3 | 0.3 | 0.3 | 0.3 | 0.3 | 0.3 | 0.3 | 0.3 | 0.3 | 0.3 |
| | Phenoxyethanol | 0.3 | 0.3 | 0.3 | 0.3 | 0.3 | 0.3 | 0.3 | 0.3 | 0.3 | 0.3 |
| | Chlorphenesin | 0.1 | 0.1 | 0.1 | 0.1 | 0.1 | 0.1 | 0.1 | 0.1 | 0.1 | 0.1 |
| Water | Water | qsp 100 | qsp 100 | qsp 100 | qsp 100 | qsp 100 | qsp 100 | qsp 100 | qsp 100 | qsp 100 | qsp 100 |

*Disodium Cocoyl Glutamate:Sodium Cocoyl Glutamate = 4:1

[Evaluations]
(Aspect)

100 g of each of the compositions according to Examples 1-7 and Comparative Examples 1-10 was charged into a transparent glass bottle, and the aspect of each composition was visually evaluated in accordance with the following criteria.

T (Transparent): The aspect was transparent (no phase separation was observed).

S (Separated): Phase separation was observed.

The results are shown in Tables 3 and 4.

For the compositions with the aspect of "separated", subsequent evaluations were skipped. Thus, the compositions according to Comparative Examples 1-5 and 7-9 were not subjected to the subsequent evaluations because they were "separated".

Examples 6 and 10 was put in an amount of 1.6 g (2 push from the pump former dispenser as mentioned above), circulated with two fingers (middle and index finger) in circular way with 40 times, and rinsed off with water for 10 seconds, followed by being checked in terms of how much amount of the mascara remains on the forearm with scoring in accordance with the following criteria.

5: Most of mascara is removed
4: Moderately mascara is removed
3: Slightly mascara is removed.
2: Very slightly mascara is removed.
1: All mascara remains on the forearm.

The scores were averaged. The results are shown in Tables 3 and 4.

(Easiness of Rinsing)

2.4 g (3 push from the pump former dispenser as mentioned above) of each of the compositions according to Examples 1-7 and Comparative Examples 6 and 10 was applied on the face of 5 panelists. After massaging for 20 seconds by hand, the composition was rinsed off by water for 10 seconds. Easiness of rinsing was evaluated during rinsing off. Specifically, the speed of rinsing was evaluated in accordance with the following criteria.

5: Very Quick
4: Quick
3: Fair
2: Slow
1: Very Slow

The scores were averaged. The results are shown in Tables 3 and 4.

(Fresh Feeling During Use)

When evaluating the easiness of rinsing as explained above, freshness was also evaluated during applying each composition and also rinsing it from the face, in accordance with the following criteria.

5: Very Fresh
4: Fresh
3: Fair
2: Not Fresh
1: Not Fresh At All

The scores were averaged. The results are shown in Tables 3 and 4.

(Eye Discomfort During Use)

When evaluating the easiness of rinsing as explained above, eye discomfort was also evaluated during applying each composition and also rinsing it from the face, in accordance with the following criteria.

5: Unacceptable Eye Discomfort
4: Strong Eye Discomfort
3: Moderate Eye Discomfort
2: Weak Eye Discomfort
1: Slight Eye Discomfort The scores were averaged. The results are shown in Tables 3 and 4.

TABLE 3

|  | Ex. 1 | Ex. 2 | Ex. 3 | Ex. 4 | Ex. 5 | Ex. 6 | Ex. 7 |
|---|---|---|---|---|---|---|---|
| Aspect | T | T | T | T | T | T | T |
| Foam | 5.0 | 5.0 | 5.0 | 5.0 | 5.0 | 5.0 | 5.0 |
| Removability of Water-Proof Mascara | 5.0 | 5.0 | 5.0 | 5.0 | 5.0 | 5.0 | 5.0 |
| Easiness of Rinsing | 5.0 | 5.0 | 5.0 | 5.0 | 5.0 | 5.0 | 5.0 |
| Fresh Feeling During Use | 5.0 | 5.0 | 5.0 | 5.0 | 5.0 | 4.5 | 4.5 |
| Eye Discomfort During Use | 1.0 | 1.0 | 1.0 | 1.5 | 1.0 | 1.0 | 1.0 |

TABLE 4

|  | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 |
|---|---|---|---|---|---|---|---|---|---|---|
| Aspect | S | S | S | S | S | T | S | S | S | T |
| Foam | — | — | — | — | — | 5.0 | — | — | — | 3.0 |
| Removability of Water-Proof Mascara | — | — | — | — | — | 2.0 | — | — | — | 4.0 |
| Easiness of Rinsing | — | — | — | — | — | 5.0 | — | — | — | 5.0 |
| Fresh Feeling During Use | — | — | — | — | — | 5.0 | — | — | — | 5.0 |
| Eye Discomfort During Use | — | — | — | — | — | 1.0 | — | — | — | 1.0 |

Examples 1-7 demonstrate that a composition according to the present invention, which includes a combination of the ingredients (a) to (e) explained above, is stable and capable of forming good form, and can remove make-up well. Examples 1-7 also demonstrate that a composition according to the present invention, which includes a combination of the ingredients (a) to (e) explained above, can provide fresh feeling during use without eye discomfort.

Comparative Examples 1 and 2 demonstrates that the ingredient (b) is necessary for providing a stable composition.

Comparative Examples 3 and 4 demonstrate that the use of oil other than the ingredient (a), without the ingredient (a), negatively affects stability.

Comparative Example 5, 7 and 8 demonstrate that the ingredients (d) and (e) are necessary for providing a stable composition.

Comparative Example 9 demonstrates that the ingredient (c) is also necessary for providing a stable composition.

Comparative Example 6 demonstrates that an oil is necessary to provide good removability of make-up.

Comparative Example 10 demonstrates that an amphoteric surfactant is necessary to provide form with good quality.

The invention claimed is:

1. A composition, comprising:
(a) at least one ether oil;
(b) at least one amphoteric surfactant chosen from ($C_8$-$C_{24}$) alkyl betaines, ($C_8$-$C_{24}$) alkylamido ($C_1$-$C_6$) alkylbetaines, and mixtures thereof;
(c) at least one anionic: surfactant selected from glutamates, glycinates and mixtures thereof;
(d) at least one polyglyceryl fatty acid ester, wherein all of the (d) at least one polyglyceryl fatty acid ester consists of at least one polyglyceryl fatty acid ester having a Hydrophilic Lipophilic Balance (HLB) value of from 7.0 to 16.0; and
(e) at least one alkylpolyglycoside,
wherein
the composition further comprises (f) at least one polyol with 5 or more carbon atoms selected from the group consisting of pentylene glycol, hexylene glycol and mixtures thereof, or phenoxyethanol,
the (e) alkylpolyglycoside is a compound of formula (I):

$$R(O)(G)_x \qquad (I)$$

in which the radical R is a linear or branched $C_{10}$-$C_{22}$ alkyl radical, x is 1 and G is a saccharide residue chosen from the group consisting of glucose, dextrose, saccharose, fructose, galactose, maltose, maltotriose, lactose, cellobiose, mannose, ribose, dextran, talose, allose, xylose, levoglucan, cellulose and starch, an amount of the (a) ether oil is 0.1% to 20% by weight, relative to the total weight of the composition, an amount of the (b) amphoteric surfactant is 0.1% to 20% by weight, relative to the total weight of the composition, an amount of the (c) anionic surfactant is 0.01% to 15% by weight, relative to the total weight of the composition, an amount of the (d) polyglyceryl fatty acid ester is 0.1% to 20% by weight, relative to the total weight of the composition, and an amount of the (e) alkylpolyglycoside is 0.01% to 15% by weight, relative to the total weight of the composition.

2. The composition according to claim 1, wherein the ether oil is selected from the group consisting of dicaprylyl ether, dicapryl ether, dilauryl ether, diisostearyl ether, dioctyl ether, nonyl phenyl ether, dodecyl dimethylbutyl ether, cetyl dimethylbutyl ether, cetyl isobutyl ether, and mixtures thereof.

3. The composition according to claim 1, wherein the (a) ether oil is present in the composition in an amount ranging from 1% to 15% by weight with respect to the total weight of composition.

4. The composition according to claim 1, wherein the (b) amphoteric surfactant is chosen from coco betaine, cocamidopropyl betaine, and mixtures thereof.

5. The composition according to claim 1, wherein the (b) amphoteric surfactant is present in the composition in an amount ranging from 1% to 15% by weight with respect to the total weight of the composition.

6. The composition according to claim 1, wherein the (c) anionic surfactant is present in the composition in an amount ranging from 0.1% to 10% by weight with respect to the total weight of the composition.

7. The composition according to claim 1, wherein the (d) polyglyceryl fatty acid ester has a polyglyceryl moiety derived from 2 to 10 glycerins.

8. The composition according to claim 1, wherein the (d) polyglyceryl fatty acid ester is present in the composition in an amount ranging from 1% to 15% by weight with respect to the total weight of the composition.

9. The composition according to claim 1, wherein the G in the formula (I) is a glucose residue.

10. The composition according to claim 1, wherein the (e) alkylpolyglycoside is present in the composition in an amount ranging from 0.05% to 10% by weight with respect to the total weight of the composition.

11. The composition according to claim 1, wherein the composition is a cosmetic composition.

12. A cosmetic product capable of forming a volume-expanded composition, comprising:
  the composition according to claim 1; and
  a volume-expanded composition dispenser, for delivering the composition in the form of a volume-expanded composition.

13. A cosmetic process for cleansing a keratin substance, comprising applying the composition according to claim 1 to the keratin substance.

14. The composition according to claim 1, wherein the (f) at least one polyol is synthetic.

* * * * *